(12) United States Patent
Baker et al.

(10) Patent No.: US 6,355,438 B1
(45) Date of Patent: Mar. 12, 2002

(54) METHOD FOR QUANTITATING OLIGONUCLEOTIDES

(75) Inventors: Brenda F. Baker; Zhengrong Yu, both of Carlsbad; Janet M. Leeds, Encinitas, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/711,050

(22) Filed: Nov. 10, 2000

Related U.S. Application Data

(60) Provisional application No. 60/165,184, filed on Nov. 12, 1999.

(51) Int. Cl.[7] .......................... C12Q 1/68; C07H 19/00; C07H 21/00; C07H 21/02; C07H 21/04
(52) U.S. Cl. .................. 435/6; 435/91.1; 435/91.2; 536/22.1; 536/23.1; 536/24.3; 536/24.33
(58) Field of Search .............. 435/6, 91.1, 91.2; 536/22.1, 23.1, 24.3, 24.33
(58) Field of Search .................................... eb

(56) References Cited

U.S. PATENT DOCUMENTS

| | | | | |
|---|---|---|---|---|
| 4,840,892 A | * | 6/1989 | Adams et al. ............... | 435/5 |
| 5,637,464 A | | 6/1997 | Cohen et al. ............... | 435/6 |
| 5,843,669 A | | 12/1998 | Kaiser et al. ............... | 435/6 |
| 5,846,717 A | | 12/1998 | Brow et al. ............... | 435/6 |
| 5,874,283 A | | 2/1999 | Harrington et al. ...... | 435/252.3 |

OTHER PUBLICATIONS

Lyamichev et al., "Polymorphism identification and quantitative detection of genomic DNA by invasive cleavage of oligonucleotide probes", *Nature Biotech.* 1999 17:292–296.

* cited by examiner

*Primary Examiner*—Jezia Riley
(74) *Attorney, Agent, or Firm*—Licata & Tyrrell P.C.

(57) ABSTRACT

Methods and processes for quantitating the amount of oligonucleotide in a sample of bodily fluid and/or extract are provided. The methods and processes provided allow for the detection and/or localization of oligonucleotides for therapeutic and/or pharmacokinetic purposes by providing a highly sensitive assay that takes advantage of enzymes which recognize specific nucleic acid conformations and structures.

35 Claims, 3 Drawing Sheets

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 1
gcccaagctg gcatccgtca                                             20

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:Synthetic

<400> SEQUENCE: 2
gttcgaccgt aggcagt                                                17

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 3
tccgtcatcg ctcctcaggg                                             20

```
<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic

<400> SEQUENCE: 4 tttttttt                                                            9
```

METHOD FOR QUANTITATING OLIGONUCLEOTIDES

This application claims priority under 35 U.S.C. §119(e) to U.S. Provisional Application Serial No. 60/165,184, filed Nov. 12, 1999 now abandoned.

FIELD OF THE INVENTION

This invention is directed to methods for detecting oligonucleotides in samples of bodily fluids and/or extracts. Included in the invention are highly sensitive processes and methods which combine oligonucleotide capture techniques, structure-specific enzymes which recognize specific DNA/RNA configurational motifs and detection/labeling systems. These processes and methods can be used, for example, to detect, localize and quantify administered oligonucleotides in bodily fluids and extracts taken from patients undergoing antisense oligonucleotide therapy. Further uses for this invention are for studying the pharmacokinetic properties of oligonucleotides in animal models.

BACKGROUND OF THE INVENTION

Detection of specific nucleic acid sequences present in a cell, group of cells, or in solution is generally known in the art. Southern (J.Mol.Biol. 98:503–527 (1975)) teaches detection of specific sequences among DNA fragments separated by gel electrophoresis using "blotting" or transfer of the DNA fragments to a membrane, followed by hybridization of denatured DNA fragments with radioactive probes and autoradiography. This procedure has been extended to the detection of RNA molecules extracted from cells or tissues. Further improvements have involved faster and more quantitative "dot-blotting" procedures to detect DNA or RNA from tissues or cells.

Various methods are known in the art which may be used to detect and characterize specific nucleic acid sequences and sequence changes. These methods must be able to create detectable signals from a very low copy number of the sequence of interest. Example approaches for detecting nucleic acids are; capillary gel electrophoresis (CGE), as described by Cohen et al. U.S. Pat. No. 5,420,265, signal amplification technology, such as polymerase chain reaction (U.S. Pat. Nos. 4,683,195 and 4,683,202 to Mullis and Mullis et al.) or ligase chain reaction (described by Barany, Proc.Natl.Acad.Sci., 88:189 (1991)), and direct detection technology, such as Southern and Northern Blotting.

Recently, considerable interest has been generated in the development of synthetic oligonucleotides as therapeutic agents. These antisense molecules and approaches to using them have been reviewed in Agarwal, Trends in Biotechnology 10:152–158 (1991). For an antisense therapeutic to be effective, the oligonucleotide must be introduced/administered to a patient and must reach the specific nucleic acid target for which it was designed. Consequently, there is a need to be able to detect oligonucleotide drugs in bodily fluids and extracts. In animal models, radio-labeled oligonucleotides have been administered to the subject and the distribution of the oligonucleotides within the body has been assessed by extraction of the oligonucleotides followed by autoradiography (Agarwal et al., Proc. Natl. Acad. Sci. 88:7595–7599 (1991)). A common aspect of current procedures is the detection of large DNA or RNA molecules (>100 bp). Due to the small size (20–30 bp) of oligonucleotides used for antisense therapeutics special problems relating to their detection exist, such as for example nonspecific binding or the absence of binding to probes producing false negatives/positives.

Lyamichev et al., Nature Biotechnology 17:292–296 (1999) describe an approach using enzymes responsible for removing the unpaired segments of DNA that arise during DNA synthesis, wherein at the 3' end of a growing upstream oligonucleotide the sequence at the 5' end of a downstream oligonucleotide is displaced. In this approach, enzymes, such as eubacterial Pol A DNA polymerases, 5' to 3' exonuclease from calf, the 5' nucleases associated with bacteriophage T5, FEN1, RAD2, and xeroderma pigmentosum-complementation group G endonuclease homologs from eukaryotes, are used to remove the cleavable flaps (redundant non-hybridized single stranded nucleic acid portion on the 5' end of the downstream segment) created by introducing an upstream oligonucleotide, getting incomplete hybridization, and not extending the primer. Lyamichev et al., describe detection of DNA targets in complex mixtures at sub-attomole levels using this approach.

Lyamichev et al., show that FEN1 nuclease can be used to detect and characterize target DNAs. By adding overlapping pairs of oligonucleotide probes complementary to a predetermined region of target DNA, the cleavage of the downstream probe's overhanging flap becomes a sensitive indicator of the presence of a target sequence. Multiple copies of the downstream oligonucleotide probe can be cleaved for each target sequence without temperature cycling, which allows amplification of the cleavage signal and also allows quantitative detection of target DNA. By using FEN1 nuclease and fluorescence labeled signal probes, Lyamichev et al. demonstrate that cycling of signal probes can occur when the reaction is carried out at temperatures near the melting temperature of the signal probe. Under these conditions, individual signal probes occupy their complementary site on the DNA target only briefly, allowing for frequent probe exchange (when performed under conditions with excess signal probe) thereby allowing amplification without temperature cycling. Further examples and uses of this approach are described in Dahlberg et al., U.S. Pat. No. 5,888,789 (1999), Kaiser et al., U.S. Pat. No. 5,843,669 (1998) and Dahlberg et al., U.S. Pat. No. 5,837,450. The various nucleases described by Lyamichev, Dahlberg, and Kaiser have been disclosed in Harrington et al., U.S. Pat. No. 5,874,283 (1999) and Dahlberg et al., U.S. Pat. No. 5,614,402.

U.S. Pat. No. 5,637,464 discloses a method for detecting a target oligonucleotide by contacting a sample comprising the oligonucleotide with a labeled primer and an unlabeled helper oligonucleotide which are complementary to the target. Once hybridized, the primer and helper oligonucleotides are joined by DNA ligase.

Both the detection and characterization of specific nucleic acid sequences and sequence changes have been utilized to determine the presence of viral or bacterial nucleic acid sequences indicative of an infection. Further uses of such approaches have allowed for the detection of the presence of variants or alleles of mammalian genes associated with disease, the identification of the source of nucleic acids found in forensic samples, as well as in paternity determinations.

Each of the preceding articles and/or patents describe approaches for detecting and/or characterizing deoxyribo and ribo- nucleic acid molecules. There has been and continues to be a long-felt need for the design of sensitive methods or processes for detecting oligonucleotide compounds, such as antisense therapeutics. Highly sensitive methods would be useful for determining the concentrations of oligonucleotide therapeutics in animal models and/or in the clinic. Further uses would be to study the pharmacokinetic properties of oligonucleotide therapeutics in animal models and/or in the clinic.

SUMMARY OF THE INVENTION

The present invention relates to methods and processes for detecting oligonucleotides in bodily fluids and extracts. The methods and processes are particularly useful for quantifying administered modified or unmodified oligonucleotides and/or investigating the pharmacokinetics of a modified or unmodified oligonucleotide compound.

One embodiment of the present invention is a method for detecting or quantitating an oligonucleotide in a bodily fluid or extract, comprising the steps of: contacting the fluid or extract with a probe complementary to the oligonucleotide to form a hybrid, wherein the probe comprises a region at one of its ends which does not hybridize to the oligonucleotide, so that a duplex or hybrid is formed; contacting the hybrid with an enzyme and a detectable label, wherein the enzyme directs the incorporation of the label into the oligonucleotide opposite the region of the probe which does not hybridize to the oligonucleotide; and detecting the label, wherein the presence of the label indicates the presence of the oligonucleotide. Preferably, the body fluid is plasma. Advantageously, the oligonucleotide comprises at least one phosphorothioate linkage. In one aspect of this preferred embodiment, the oligonucleotide comprises a modification at the 2'position of at least one sugar moiety. Preferably, the 2'modification is a 2'-O-methoxyethyl modification. Advantageously, the oligonucleotide comprises at least one modified base. Preferably, the modified base is 5-methylcytosine. In one aspect of this preferred embodiment, the label is calorimetric, radioactive, chemiluminescent, enzymatic or fluorescent. Advantageously, the label is digoxigenin. Preferably, the enzyme is DNA polymerase. In one aspect of this preferred embodiment, the oligonucleotide is exogenously administered.

The present invention also provides a method for detecting or quantitating an oligonucleotide in a bodily fluid or extract, comprising the steps of: contacting the fluid or extract with a capture probe complementary to-the oligonucleotide to form a hybrid, wherein the capture probe comprises a region at one of its ends which does not hybridize to the oligonucleotide; contacting the hybrid with a labeled detection probe complementary to the region of the capture probe which does not hybridize to the oligonucleotide in the presence of an enzyme capable of ligating the oligonucleotide and the detection probe; and detecting the label, wherein the presence of the label indicates the presence of the oligonucleotide. Preferably, the body fluid is plasma. Advantageously, the oligonucleotide comprises at least one phosphorothioate linkage. In one aspect of this preferred embodiment, the oligonucleotide comprises a modification at the 2' position of at least one sugar moiety. Preferably, the 2' modification is a 2'-O-methoxyethyl modification. Advantageously, the oligonucleotide comprises at least one modified base. Preferably, the modified base is 5-methylcytosine. In one aspect of this preferred embodiment, the label is calorimetric, radioactive, chemiluminescent, enzymatic or fluorescent. Preferably, the label is digoxigenin. In another aspect of this preferred embodiment, the enzyme is DNA ligase. Advantageously, the oligo nucleotide is exogenously administered.

Another embodiment of the present invention is a method for detecting or quantitating an oligonucleotide in a bodily fluid or extract, comprising the steps of: contacting the fluid or extract with a capture probe complementary to the oligonucleotide and a second probe, wherein the capture probe comprises a detectable marker and a portion which binds to the oligonucleotide, and wherein the second probe comprises a first portion which binds to the detectable marker and a second portion which produces an overhanging flap upon binding to the oligonucleotide to form a complex; contacting the complex with a nuclease to cleave the flap; and detecting the flap. Preferably, the body fluid is plasma. Advantageously, the oligonucleotide comprises at least one phosphorothioate linkage. In one aspect of this preferred embodiment, the oligonucleotide comprises a modification at the 2' position of at least one sugar moiety. Preferably, the 2' modification is a 2'-methoxyethyl modification. Advantageously, the oligonucleotide comprises at least one modified base. Preferably, the modified base is 5-methylcytosine. In one aspect of this preferred embodiment, the nuclease is eubacterial polA DNA polymerase, 5' to 3' exonuclease, 5' nuclease associated with bacteriophage T5, FEN1, RAD2 or xeroderma pigmentosum-complementation group G endonuclease homologs from eukaryotes. Preferably, the oligonucleotide is exogenously administered.

Further aspects of the invention are described within the description of the preferred embodiments. The summary of the invention described above is not limiting and other features and advantages of the invention will be apparent from the following detailed description of the invention and from the claims.

DETAILED DESCRIPTION OF THE INVENTION

Figure 1:
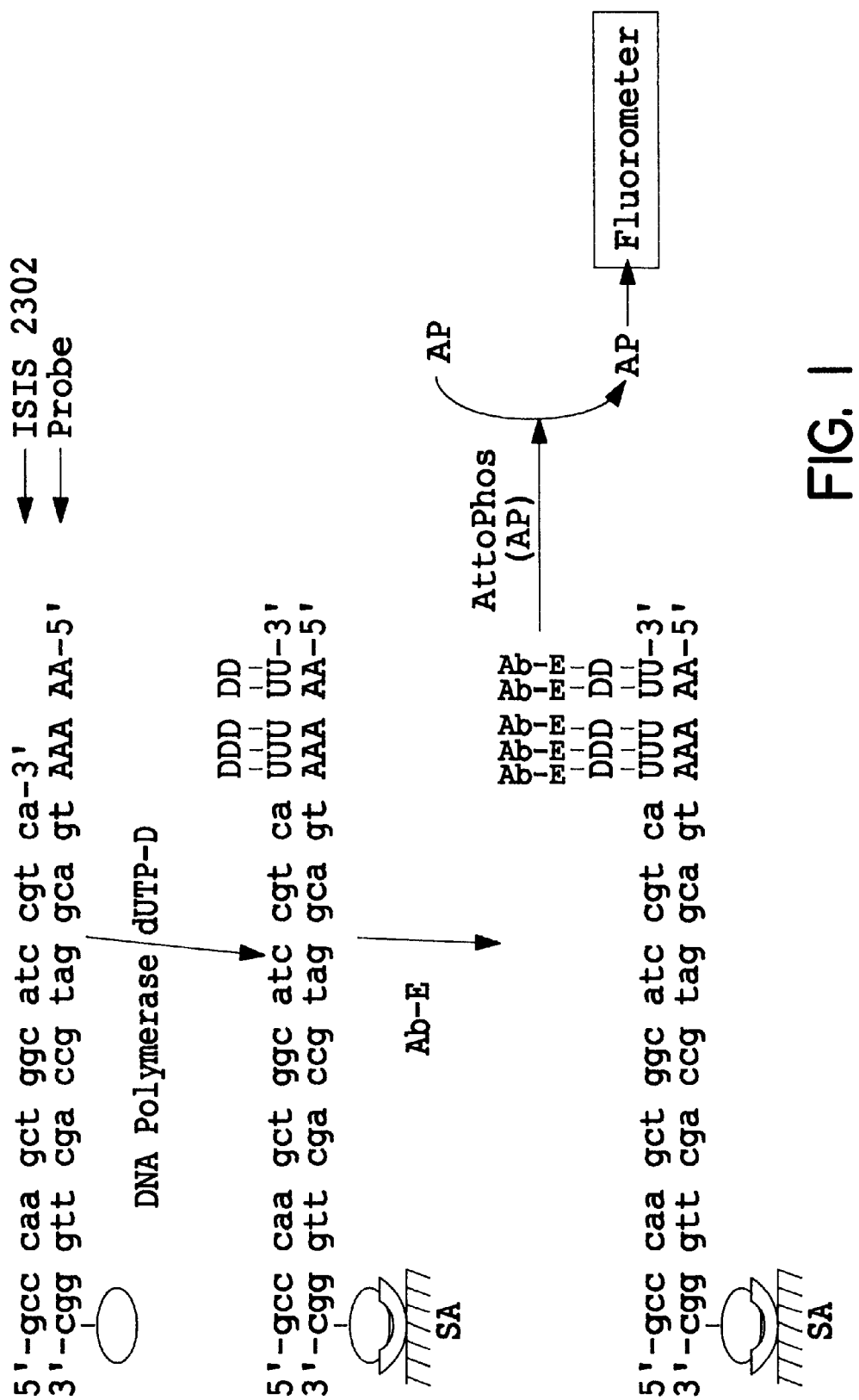
FIG. 1 is a diagram showing the steps in a method for quantitative detection of a phosphorothioate oligodeoxynucleotide, ISIS 2302, by ELISA assay after digoxigenin labeling of the ISIS 2302 using DNA polymerase.

The present invention provides highly sensitive methods for detecting oligonucleotides, particularly modified oligonucleotides, in a bodily fluid and/or extract. In one embodiment, the oligonucleotide is exogenously administered to an animal, preferably a mammal, more preferably a human. Current methods for detecting and or quantitating oligonucleotides such as capillary gel electrophoresis (CGE) provide increased detection of small molecules when compared to traditional slab-gel electrophoresis. CGE has been used for size-based separation of biological macromolecules such as DNA restriction fragments, proteins and oligonucleotides. The methods described herein provide a 500–1000 fold increase in the sensitivity of detection of oligonucleotides in biological samples when compared to methods such as CGE.

In one embodiment, an oligonucleotide which has been administered to a subject is detected by obtaining a sample of bodily fluid and/or extract from the subject and contacting the sample with a probe and a structure specific nuclease. The if: capture probe comprises a detectable marker which allows for detection by interacting with a detectable label. Detection and quantitation are via the detectable label's binding partner(s) and/or substrate(s). In one embodiment, the oligonucleotide comprises one or more modifications.

In the context of this invention, the term "oligonucleotide" refers to an oligomer or polymer of ribonucleic acid or deoxyribonucleic acid. In one embodiment, the oligonucleotide is an antisense oligonucleotide. The term "oligonucleotide" includes oligonucleotides composed of naturally-occurring nucleobases, sugars and covalent intersugar (backbone) linkages as well as oligonucleotides having non-naturally-occurring portions which function similarly. Such "modified" or substituted oligonucleotides are often preferred over native forms because of desirable properties such as, for example, enhanced cellular uptake, enhanced binding to target, increased stability in the presence of nucleases and an increase in bioavailability.

Within the concept of "modified" oligonucleotides, the present invention also includes detection of compositions employing oligonucleotide compounds which are chimeric compounds. "Chimeric" oligonucleotide compounds or "chimeras," in the context of this invention, are nucleic acid compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or consist of an oligomeric sequence known to modify complement activation. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy- substituted), or vice-versa.

A number of chemical modifications to oligonucleotides that confer greater oligonucleotide:RNA duplex stability have been described by Freier et al. (Nucl. Acids Res., 1997, 25, 4429). Such modifications are preferred for the RNase H-refractory portions of chimeric oligonucleotides and may generally be used to enhance the affinity of an antisense compound for a target RNA.

Chimeric modified oligonucleotide compounds may be formed as composite structures of two or more oligonucleotides, modified oligonucleotides, oligonucleosides and/or oligonucleotide mimetics as described above, ligand-oligonucleotide constructs, or complement protein-oligonucleotide constructs as described herein. Some of these compounds have also been referred to in the art as hybrids or gapmers. Representative United States patents that teach the preparation of some of these hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,955,589 and 5,700,922, certain of which are commonly owned, and each of which is herein incorporated by reference.

Modifications to an oligonucleotide molecule can alter the concentration of the molecule required to elicit the effect for which the molecule is designed. Non limiting examples include varying the amount of phosphorothioate linkages in the oligonucleotide or altering the oligonucleotide base composition and chemistry such as in the preparation of CpG oligodeoxynucleotides as described by Krieg et al., Nature 1995 374:546–549, Weiner et al., Proc. Natl. Acad. Sci. USA 1997 94:10833–10837, Liu, HM et al., Blood 1998 15;92(10):3730–3736, Boggs, RT et al., Antisense Nucleic Acid Drug Dev 1997 7(5):461–471, and Kline et al., J.Immunol 1998 15;160(6):2555–2559.

Also detectable by the methods of the invention are compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (U.S. Pat. No. 5,587,361) and those having substantially chirally pure (Sp or Rp) alkylphosphonate, phosphoramidate or phosphotriester linkages (U.S. Pat. Nos. 5,212,295 and 5,521,302).

Specific examples of some preferred modified oligonucleotides detectable by the present invention include those containing phosphorothioates (P=S oligonucleotides), phosphotriesters, methyl phosphonates, short chain alkyl or cycloalkyl intersugar linkages or short chain heteroatomic or heterocyclic intersugar linkages. oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Examples of modified oligonucleotide backbones include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Additional examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application. In other example oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., Science, 1991, 254, 1497–1500.

Additional examples are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Oligonucleotides having morpholino backbone structures of the above-referenced U.S. Pat. No. 5,034,506, are also detectable using methods of the present invention.

Modified oligonucleotides may also contain one or more substituted sugar moieties. Example oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Non limiting examples are O[($CH_2$)$_n$O]$_m$$CH_3$, O($CH_2$)$_n$O$CH_3$, O($CH_2$)$_n$N$H_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. Other examples comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2$$CH_3$, O$NO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Other example modifications include 2'-methoxyethoxy (2'—O—$CH_2$$CH_2$O$CH_3$, also known as 2'-O-(2-methoxyethyl) or 2'-MOE) (Martin et al., Helv. Chim. Acta, 1995, 78, 486–504) i.e., an alkoxyalkoxy group. Modifications which include 2'-dimethylaminooxyethoxy, i.e., a O($CH_2$)$_2$ON($CH_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

Additional example modifications include 2'-methoxy (2'-O—$CH_3$), 2'-aminopropoxy (2'—O$CH_2$$CH_2$$CH_2$N$H_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science and Engineering, pages 858–859, Kroschwitz, J.I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B. , ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6–1.2° C. god (Sanghvi, Y. S., Crooke, S. T. and Lebleu, B., eds., Antisense Research and Applications, CRC Press, Boca Raton, 1993, pp. 276–278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of oligonucleotides detectable by the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553–6556), cholic acid (Manoharan et al., Bioorg. Med. Chem. Let., 1994, 4, 1053–1060), a thioether, e.g., hexyl-S-tritylthiol (Manoharan et al., Ann. N.Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., Biochimie, 1993, 75, 49–54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651–3654; Shea et al., Nucl. Acids Res., 1990, 18, 3777–3783), a polyamine or a polyethylene glycol chain (Manoharan et al., Nucleosides & Nucleotides, 1995, 14, 969–973), or adamantane acetic acid (Manoharan et al., Tetrahedron Lett., 1995, 36, 3651–3654), a palmityl moiety (Mishra et al., Biochim. Biophys. Acta, 1995, 1264, 229–237), or an octadecylamine or hexylamino-carbonyl-oxycholesterol moiety (Crooke et al., J. Pharmacol. Exp. Ther., 1996, 277, 923–937.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide.

Further examples of modifications for the oligonucleotides detectable by the present invention involve chemically linking to the oligonucleotide one or more glipophilic moieties which enhance the cellular uptake of the oligonucleotide. Such lipophilic moieties may be linked to an oligonucleotide at several different positions on the oligonucleotide. Some non-limiting example positions include the 3' position of the sugar of the 3' terminal nucleotide, the 5' position of the sugar of the 5' terminal nucleotide, and the 2' position of the sugar of any nucleotide. The N6 position of a purine nucleobase may also be utilized to link a lipophilic moiety to an oligonucleotide of the invention (Gebeyehu, G., et al., Nucleic Acids Res., 1987, 15, 4513). Such lipophilic moieties include but are not limited to a cholesteryl moiety (Letsinger et al., Proc. Natl. Acad. Sci. USA, 1989, 86, 6553), cholic acid (Manoharan et al., Bioorg. Med. Chem. Let., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEES Lett., 1990, 259, 327; Svinarchuk et al., Biochimie, 1993, 75, 49), a phospholipid, e.g., di-hexadecyl-rac-glycerol or triethylammonium 1,2-di-o-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylamino-carbonyl-oxycholesterol moiety (Crooke et al., J. Pharmacol. Exp. Ther., 1996, 277, 923). Oligonucleotides comprising lipophilic moieties, and methods for preparing such oligonucleotides, as disclosed in U.S. Pat. Nos. 5,138,045, 5,218,105 and 5,459,255, the contents of which are hereby incorporated by reference in their entirety.

In other examples the compound to be detected may be a ligand conjugated oligomeric compound having improved pharmacokinetic properties. Such oligomeric compounds are prepared having covalently attached ligands or proteins that bind reversibly to or interact with one or more serum, vascular or cellular proteins. This reversible binding is expected to decrease urinary excretion, increase serum half life and greatly increase the distribution of oligomeric compounds thus conjugated. The binding of particular drugs to plasma proteins has been previously shown to enhance the disposition and efficacy of drugs (Herve et al., Clin. Pharmacokinet., 1994, 26:44).

Many drugs reversibly bind to plasma proteins. A representative list, which is not meant to be inclusive, includes: aspirin, warfarin, phenylbuta-zone, ibuprofen, suprofen, fenbufen, ketoprofen, (S)-(+)-pranoprofen, carprofen, dansylsarcosine, 2,3,5-triiodobenzoic acid, flufenamic acid, folinic acid, benzothiadiazides, chlorothiazide, diazepines (such as for example fludiazepam and diazepam) indomethacin, barbiturates (such as for example quinalbarbitone), cephalosporins, sulfa drugs, antidiabetics (such as for example tolbutamide), antibacterials (such as for example a group of quinolones; nalidixic acid and cinoxacin) and several antibiotics. Serum albumin is the most important protein among all plasma proteins for drug binding, although binding to other proteins (for example, macroglobulin G2, immunoglobulins, lipoproteins, alpha-1-acid glycoprotein, thrombin) is also important.

Ligands such as the above drugs that bind serum, vascular or cellular proteins may be attached via an optional linking moiety to one or more sites on an oligonucleotide to be administered to a subject and detected in accordance with the present invention. These sites include one or more of, but are not limited to, the 2'-position, 3'-position, 5'-position, the internucleotide linkage, and a nucleobase atom of any nucleotide residue. The attachment of ligands to such structures can be performed, according to some preferred embodiments of the invention, using a linking group, or without the use of such a linking group. Example linking groups include, 6-aminoalkoxy linkers, 6-aminoalkylamino linkers, cysteamine, heterobifunctional linkers, homobifunctional linkers, and a universal linker (derived from 3-dimethoxytrityloxy-2-aminopropanol). A particularly preferred linking group for the synthesis of ligand conjugated oligonucleotides of the invention is a 6-aminohexyloxy group. A variety of heterobifunctional and homobifunctional linking moieties are available from Pierce Co. (Rockford, Ill.). Such heterobifunctional and homobifunctional linking moieties are particularly useful in conjunction with the 6-aminoalkoxy and 6-aminoalkylamino moieties to form extended linkers useful for linking ligands to a nucleoside. Further useful linking groups that are commercially available are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, while the 3'-Amino-Modifier is also available from Clontech Laboratories Inc. (Palo Alto, Calif.). In addition, a nucleotide analog bearing a linking group pre-attached to the nucleoside is commercially available from Glen Research Corporation under the trade name "Amino-Modifier-dT." This nucleoside-linking group reagent, a uridine derivative having an [N(7-trifluoroacetylaminoheptyl) 3-acrylamido] substituent group at the 5 position of the pyrimidine ring, is synthesized as per the procedure of Jablonski et al. (Nucleic Acid Research, 1986, 14:6115).

Ligand conjugated oligonucleotides may be synthesized by the use of an oligonucleotide that bears a pendant reactive functionality such as that derived from the attachment of a linking molecule onto the oligonucleotide. This reactive oligonucleotide may be reacted directly with commercially available ligands, ligands that are synthesized bearing a variety of protecting groups, or ligands that have a linking moiety attached thereto.

The oligonucleotides detectable in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta, 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

By the terms "administered" or "administered" is meant providing to a subject an oligonucleotide. Administration may be topical (including ophthalmic, vaginal, rectal, intranasal, epidermal and transdermal), oral or parenteral, needle injection, needle-free injection as in, for example, an injection using a device like the MEDI-JECTOR™, and by aliquots using a pipette. Parenteral administration includes intravenous drip or infusion, subcutaneous, intraperitoneal or intramuscular injection, pulmonary administration, e.g., by inhalation or insufflation, or intracranial, e.g., intrathecal or intraventricular, administration. Modes of administering oligonucleotides are disclosed in U.S. Pat. No. 6,083,923, the entire contents of which are incorporated herein by reference.

Formulations for topical administration may include transdermal patches, ointments, lotions, creams, gels, drops, suppositories, sprays, liquids and powders.

Compositions for oral administration include powders or granules, suspensions or solutions in water or non-aqueous media, capsules, sachets or tablets. Thickeners, flavoring agents, diluents, emulsifiers, dispersing aids or binders.

Compositions for parenteral administration may include sterile aqueous solutions which may also contain buffers, diluents and other suitable additives. Methods for providing a compound to a subject are well known and are not considered limiting aspects of the present invention. Furthermore, the site or target of administration is also not considered a limiting aspect to the present invention.

"Subject" as used herein refers to a mammal that has been administered an oligonucleotide. Non-limiting examples of mammals of the invention include rodent, lagomorph, porcine, canine, feline, and primate. In a preferred embodiment the mammal is a primate and most preferably the mammal is a human.

As used herein "detect" or "detected" means the instrumental measurement or visual observation of the detectable label as indicative of the presence of the synthetic oligonucleotide in the obtained bodily fluid and/or extract sample. Various detectable labels have been discussed in the art and each label has a well-known protocol for its use and detection. Label detection protocols include, but are not limited to, sprectrophotometric measurement, fluorometric measurement, autoradiographic measurement, calorimetric measurement, visual observation, chemiluminescent measurement, electrochemical measurement and the like.

By the phrase "obtain(ing) a sample" is meant the extraction or separation of a bodily fluid and/or extract from the subject. Approaches for obtaining, extracting, excising, lancing, dissecting, excreting, evacuating bodily fluid and/or extracts from a subject or by a subject, are well known and have been practiced or requested by nurses, physicians and research scientists. The approach used to obtain the bodily fluid and/or extract is not considered a limiting aspect of the present invention.

In the context of the present invention "bodily fluid and/or extract" refers to any bodily substance removed from the subject to be screened for the presence of the oligonucleotide. Example bodily fluid and/or extracts include, but are not limited to, homogenized tissue, organ, or bone sample.

While it is understood that some portions of the body are not readily assayed as a fluid, procedures to homogenize and prepare liquid samples from those portions are not uncommon, and are well known. The addition of water or saline to body portions which are normally not liquid is within the scope of the present invention, for example, a homogenized sample of a bone suspension, can be assayed by the methods described herein. Thus, the bodily fluid and/or extract may be prepared, or may be selected from, but not limited to, the following; tissue, bone or organ samples, serum, saliva, feces, tears, sweat, and samples of blood cells, epithelial cells, and the like.

By "probe" is meant an oligonucleotide configured and arranged to bind the target oligonucleotide molecule. In one embodiment, this target oligonucleotide has been administered to the subject. Preferably the probe is configured to contain a detectable marker. A "capture probe" is a probe containing a moiety for binding to a solid support, such as biotin, which binds strongly and specifically to streptavidin-coated solid supports such as beads, culture dishes or 96 well plates, for example, allowing "capture" of the oligonucleotide to be detected onto a solid support.

In a preferred embodiment ("elongation assay"), the probe is configured to comprise a poly A tail and is further arranged to bind to a solid support. Positive binding of the target oligonucleotide to the probe in the presence of a structure specific enzyme, such as a DNA polymerase, and a detectable marker, such as digoxigenin conjugated to dUTP, initiates elongation of the target oligonucleotide molecule and incorporation of the detectable marker into the now elongated target oligonucleotide molecule. (FIG. 1).

Detection of the oligonucleotide molecule is by binding of the digoxigenin-dUTP, to an antidigoxigenin antibody-alkaline phosphatase construct which will catalyze the formation of a detectable label.

Figure 2:
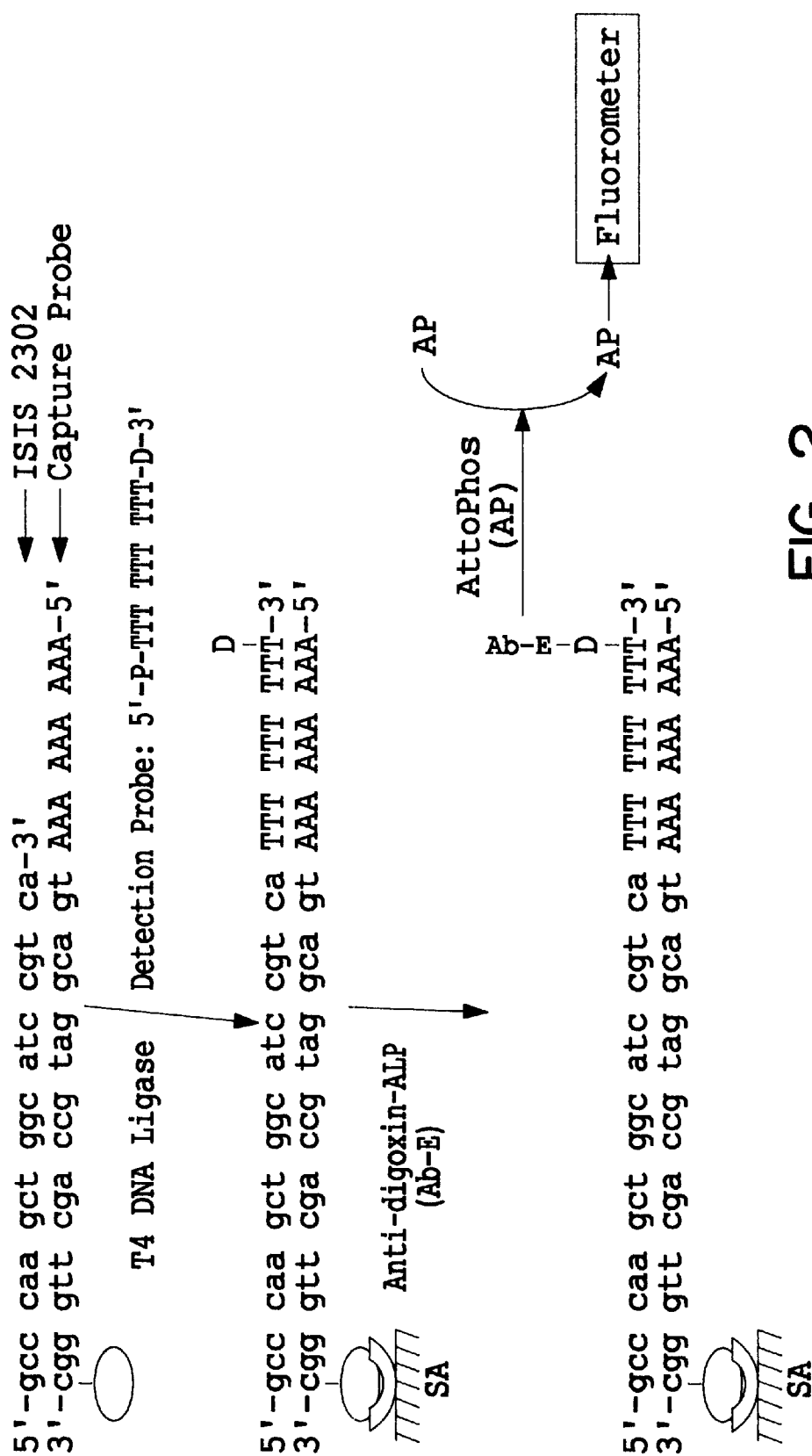
FIG. 2 is a diagram showing the steps in a method for quantitative detection of ISIS 2302 by ELISA assay after labeling of the ISIS 2302 by ligation of a digoxigenin-labeled poly(dT) detection probe.

In a further embodiment ("ligation assay"), a detection probe is prepared which comprises a detectable marker such as digoxigenin and is arranged to bind to a capture probe which is bound to a solid support. The capture probe is configured to bind both the detection probe and the oligonucleotide molecule. Both the detection probe and the administered oligonucleotide bind the capture probe in a manner so that the detection probe and oligonucleotide lie down end to end (FIG. 2). The length of the gap between the two may be 1–2 bases in length, allowing detection of n-1 or n-2 metabolites (shortened strands of the oligonucleotide molecule). In the presence of a structure specific enzyme the gap serves as a recognition site at which the enzyme ligates the detection probe and the oligonucleotide molecule together. Oligonucleotide molecules that are not ligated to a probe are not detected (FIG. 2). Detection of the oligonucleotide molecule is by the addition of anti-digoxigenin antibody conjugated to an enzyme which produces a detectable product (e.g., alkaline phosphatase and subsequent analysis of fluorescence).

In another embodiment, the capture probe contains two portions, a binding portion which is complementary to the oligonucleotide, and a detectable marker which may be another known oligonucleotide sequence (homogeneous sequence such as polyA, or heterogeneous sequence). A second probe, the flap producing probe, also contains two portions, one of which binds specifically to the detectable marker sequence in the capture probe (either via polyT or via the complement of the heterogeneous marker sequence) and a further portion which produces an overhanging "flap" upon binding of the two probes to the modified oligonucleotide. The overhanging flap portion is cleaved by a structure specific enzyme, preferably a flap endonuclease (FEN). Lyamichev et al., Nature Biotechnology 17:292–296 (1999). This method is similar to that of Lyamichev et al. but a notable difference is that the known and unknown sequences (probes versus sequence to be detected) are reversed. The "invasive probe" described in the method of Lyamichev et al. is replaced in the present method by the modified oligonucleotide to be detected. The target sequence disclosed by Lyamichev et al. (FIG. 4) is replaced in the present method by the two part capture probe, the 5' overhanging portion of which is the detectable marker. The "signal probe" disclosed by Lyamichev et al. is replaced in the present method by the flap producing probe. In preferred embodiments, the structure specific cleaving enzyme is elected from the group including, but not limited to, eubacterial Pol A DNA polymerase, 5' to 3' exonuclease, the 5' nuclease associated with bacteriophage T5, FEN1, RAD2 and xeroderma pigmentosum-complementation group G endonuclease homologs from eukaryotes.

The cleaved flap is then detected in a variety of ways known in the art, for example by incorporation of fluorescent moieties into the flap, or with the ELISA assays described herein.

"Detectable marker" as used herein refers to that component or moiety attached to a probe or a component of the probe, which is capable of interacting with and/or binding to a detectable label. In nonlimiting examples, detectable markers include nucleic acids conjugated to a member of a binding pair or substrates for enzymatic reactions such as digoxigenin, series of nucleotides which will form a flap as described herein, or a series of nucleotides of known (homogeneous or heterogeneous) sequence, e.g. polyA.

By the term "detectable label" is meant a compound and/or molecule that is observable by either visual or mechanical means. In nonlimiting examples, bifluoro-chromophores, radioactive isotopes, chemiluminescent or chromogenic labels presently available may be used as detectable labels. The detectable label and the manner by which the label is monitored are not considered to be limiting factors of the present invention. The detectable label can be part of a binding pair such as for example biotin-streptavidin, digoxigenin conjugated to alkaline phosphatase or other antigen-antibody complexes. The detectable label offers a way to determine the presence of the modified oligonucleotide via positive interaction with the probe.

Various enzymes recognize a specific nucleic acid configuration as a site chemical reaction, e.g. for cleaving nucleic acid molecules (nucleases) or as a site for adding nucleic acid molecules to an existing chain (polymerases) In one example, the enzyme is a nuclease that recognizes the unpaired segments of DNA that arise during DNA synthesis, wherein at the 3' end of a growing upstream oligonucleotide the sequence at the 5' end of a downstream oligonucleotide is displaced causing a flap of single stranded unhybridized nucleic acid molecule. In another example, the enzyme is a polymerase that recognizes the recessed 3' end of a nucleic acid duplex and elongates it by incorporating the appropriate available homologous nucleotides. In yet another example, the structure specific enzyme is a ligase that recognizes "gaps" between the ends of two nucleic acid molecules lying end to end and ligates the strands together, closing the gap.

Although the methods described herein were used to analyze particular oligonucleotides, one of ordinary skill in the art will appreciate that any desired oligonucleotide can be quantitated and analyzed using the methods described in the present invention by designing probes which are complementary to the oligonucleotide to be detected. The examples presented herein should thus be construed as illustrative and not limiting the scope of the invention.

EXAMPLES

Example 1

Detection and Quantitation of a Phosphorothioate Oligodeoxynucleotide, ISIS 2302, in Plasma Using Polymerase/ELISA Assay This assay is applied to measure total exposure in plasma following administration of oligonucleotide, for example systemic or topical administration of an oligonucleotide drug.

The oligonucleotide used was ISIS 2302 (GCC CAA GCT GGC ATC CGT CA; SEQ ID NO: 1) which is an antisense oligonucleotide targeted to human ICAM-1. This compound is currently in clinical trials for Crohn's disease, kidney transplant rejection and preclinical trials for psoriasis (topical administration).

An oligonucleotide probe having the sequence CGG GTT CGA CCG TAG GCA GT (SEQ ID NO: 2) (complementary to ISIS 2302) with a biotin molecule conjugated to the 3'-end and a poly-A tail at the 5'-end was allowed to hybridize (i.e., form duplexes) to ISIS 2302 in plasma for one hour at 37° C. and subsequently allowed to bind to a streptavidin coated plate via the biotin moiety for 30 minutes at 37° C.

DNA polymerase (Klenow fragment), digoxigenin-labeled dUTP (D-dUTP), DATP, dGTP, and dCTP were added to the plate and the mixture was incubated at 37° C. for 30 minutes. DNA Polymerase I Large (Klenow) Fragment consists of a single polypeptide chain (68 kDa) which lacks the 5'→3' exonuclease activity of intact *E. coli* DNA polymerase I, but retains its 5'→3' polymerase, 3'→5' exonuclease and strand displacement activities. The 5'→3' polymerase activity of Klenow Fragment is routinely used to fill in 5'-protruding ends with unlabeled or labeled dNTPs. As used herein, this resulted in addition of D-dUTP by the DNA polymerase only to the oligonucleotide stand of the probe/oligonucleotide duplexes, which have a 5'-polyA overhang. This is shown in FIG. 2.

After incubation, incorporated D-dUTP was detected by ELISA assay by adding an antibody conjugate construct of anti-digoxigenin and alkaline phosphatase, which catalyzed the formation of fluorescent AttoPhos™. The fluorescence intensity was determined using a Cytofluor microtiter plate reader, excitation 450/50, emission 580/50 providing a way to quantitate the total concentration of oligonucleotide compound (ISIS 2302).

Using this method it was found to be possible to detect full length oligonucleotide molecules and metabolites shortened by from one to ten nucleotides. This assay was shown to be at least five hundred times more sensitive than capillary gel electrophoresis (CGE) [Limit of Quantitation (LOQ)=10 nM], providing a linear range at oligonucleotide concentrations from 20 pM to 2000 pM (2 nM) when using 100 µl plasma.

Example 2

Inter-assay Accuracy and Precision

The ELISA assay described in Example 1 for detection of ISIS 2302 was found to have acceptable inter-assay accuracy and precision, as shown in Tables 1 and 2:

TABLE 1

Intra-day Accuracy and Precision

| ISIS 2302 Nominal Concentration | 20 pM | 50 pM | 200 pM | 1000 pM |
|---|---|---|---|---|
| Measured concentration Repetition 1 (pM) | 22.2 | 47.0 | 192 | 1109 |
| Measured concentration Repetition 2 (pM) | 18.2 | 46.6 | 204 | 1041 |
| Measured concentration Repetition 3 (pM) | 17.8 | 43.2 | 209 | 1109 |
| Measured concentration Repetition 4 (pM) | 20.0 | 48.5 | 199 | 1052 |
| Measured concentration Repetition 5 (pM) | 21.2 | 53.8 | 192 | 1124 |
| Mean | 19.9 | 47.8 | 199 | 1087 |
| SD | 1.88 | 3.85 | 7.24 | 37.7 |
| % CV* | 9.45 | 8.05 | 3.63 | 3.47 |
| % of Nominal Concentration | 99.5 | 95.6 | 99.6 | 108.7 |

*CV = coefficient of variation and is equal to (SD/Mean) × 100%.

TABLE 2

Inter-day Accuracy and Precision
Repetitions (n = 13) were done over 3 days.

| ISIS 2302 Concentration | 20 pM | 50 pM | 200 pM | 1000 pM |
|---|---|---|---|---|
| Mean | 18.9 | 46.3 | 205 | 1022 |
| SD | 2.98 | 6.87 | 12.4 | 87.0 |
| % CV* | 15.8 | 14.8 | 6.03 | 8.52 |
| % Nominal | 94.5 | 92.7 | 103 | 102 |

*CV = coefficient of variation and is equal to (SD/Mean) × 100%

Example 3

Detection and Quantitation of a Phosphorothioate Oligodeoxynucleotide, ISIS 2503, in Human Plasma Using Polymerase/ELISA Assay ISIS 2503 (TCC GTC ATC GCT CCT CAG GG; SEQ ID NO: 3) is an antisense oligonucleotide targeted to human Ha-ras. This compound is currently in clinical trials in patients with various solid tumor types. ISIS 2503 was detected in human plasma using the method described in Example 1, except that the biotinylated/polyadenylated probe was complementary to ISIS 2503 (instead of ISIS 2302). A linear range of detection of ISIS 2503 at concentrations from 5 to 1000 pM was obtained. The LOQ in human plasma was found to be 10 pM, making this assay 1000 times more sensitive than CGE for detection of oligonucleotide. The results are shown in Table 3. Experiments are replicates (n=5).

TABLE 3

Accuracy and Precision for Detection of ISIS 2503 in Human Plasma

| Compound | Nominal Conc. (pM) | Calculated Conc. (pM) | Accuracy (% of Nominal) | precision (% CV) |
|---|---|---|---|---|
| ISIS 2503 | 10 | 10.5 | 105 | 17.0 |
|  | 30 | 24.3 | 81.1 | 17.8 |
|  | 100 | 87.0 | 87.0 | 8.89 |
|  | 500 | 534 | 107 | 5.92 |

TABLE 3-continued

Accuracy and Precision for Detection of ISIS 2503 in Human Plasma

| Compound | Nominal Conc. (pM) | Calculated Conc. (pM) | Accuracy (% of Nominal) | precision (% CV) |
|---|---|---|---|---|
| n-1 | 10 | 8.3 | 83.0 | 18.3 |
|  | 30 | 37.3 | 124 | 13.9 |
|  | 100 | 110 | 110 | 11.8 |
|  | 500 | 504 | 101 | 10.4 |
| n-2 | 10 | 10.3 | 103 | 20.2 |
|  | 30 | 31.8 | 106 | 11.1 |
|  | 100 | 105 | 105 | 7.73 |
|  | 500 | 534.4 | 107 | 5.92 |
| n-3 | 10 | 8.88 | 88.8 | 13.1 |
|  | 30 | 31.3 | 104 | 7.50 |
|  | 100 | 106 | 106 | 3.39 |
|  | 500 | 503 | 101 | 2.76 |
| N-4 | 10 | 6.85 | 68.5 | 9.87 |
|  | 30 | 29.3 | 97.7 | 6.59 |
|  | 100 | 95.3 | 95.3 | 5.11 |
|  | 500 | 429 | 86.6 | 4.09 |

*CV = coefficient of variation and is equal to (SD/Mean) × 100%.

Example 4

Detection and Quantitation of a Phosphorothioate Oligodeoxynucleotide, ISIS 2302, in Plasma Using DNA Ligase/ELISA Assay As described in Example 1, the oligonucleotide test compound used was ISIS 2302 (sequence GCC CAA GCT GGC ATC CGT CA; SEQ.ID.NO: 1). As before, an oligonucleotide probe having the sequence CGG GTT CGA CCG TAG GCA GT (SEQ.ID.NO: 2) (complementary to ISIS 2302) with a biotin molecule conjugated to the 3'-end and a polyA tail at the 5'-end was allowed to hybridize to ISIS 2302 in plasma for one hour at 37° C. and subsequently allowed to bind to a streptavidin coated plate via the biotin moiety for 30 minutes at 37° C. The plate was washed four times with TBS/Tween.

Figure 4:
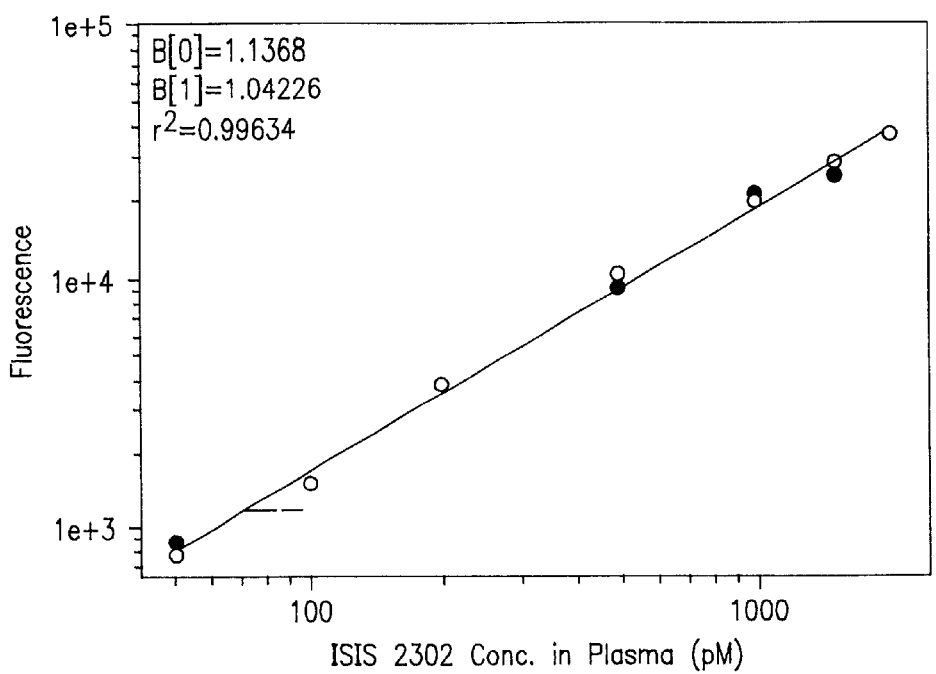
FIG. 4 is a representative calibration curve of ISIS 2302 in human plasma obtained by the ELISA/ligation assay. Each calibration point was run in duplicate.

A detection probe was prepared having the sequence 5'-TTT TTT TTT-3' (SEQ ID NO: 4) wherein the 5' end of the molecule had a phosphate group and the 3' most T was labeled with digoxigenin. This is shown in FIG. 4. 100 pM of this probe was added per well along with 0.5 units T4 DNA ligase. The ligation reaction was allowed to proceed for 30 minutes at room temperature (ligation times ranging from 30 minutes to 6 hours have been tested and found acceptable). The plate was washed in TBS, distilled water, and again in TBS. The D-dUTP on the duplexed and ligated detection probe was detected as in Examples 1 and 3 by adding an antibody conjugate construct of anti-digoxigenin and alkaline phosphatase, which catalyzed the formation of fluorescent AttoPhos™. The fluorescence intensity was determined using a Cytofluor microtiter plate reader, excitation 450/50, emission 580/50 after subtraction of fluorescence value of a control (fluorescence blank) without ISIS 2302, providing a way to quantitate the total concentration of oligonucleotide compound (ISIS 2302).

Flourescence values obtained are shown in Table 4. The same method was used to quantitate an n-1 metabolite of ISIS 2302 (19 mer) and ISIS 15839, an oligonucleotide having the sequence of ISIS2302 (SEQ ID NO: 1) with nucleotides 1–12 (at the 5' end) are deoxynucleotides and nucleotides 13–20 (3' end) are 2'-O-methoxyethyl nucleotides.

TABLE 4

Fluorescence measurements of ISIS 2302, n-1 and ISIS 15839 in plasma

| Oligo Conc. (pM) | 2302 Fluorescence | 2302 n-1 Fluorescence | 15839 Fluorescence |
|---|---|---|---|
| 10 | 275 | 216 | 597 |
| 50 | 1110 | 840 | 219 |
| 100 | 2206 | 2425 | 276 |
| 500 | 10863 | 7580 | 988 |
| 1000 | 19412 | 15493 | 1958 |
| 5000 | 36316 | 27224 | 9663 |
| 10000 | 40643 | 34262 | 12983 |

When plotted, the fluorescence values for the modified oligonucleotide ISIS 15839 gave a straight line at oligonucleotide concentrations between 100 and 10000 pM. ISIS 2302 and n-1 gave overlapping (i.e., almost identical) straight lines at concentrations from 10 to 1000 pM. It was subsequently found that the n-2 metabolite gave fluorescence readings nearly identical to the n-1 and full length ISIS 2302 oligonucleotides, but fluorescence values for n-3 and shorter were less than 10% of these. This makes this method uniquely suited to detecting and quantitating full length or nearly full-length oligonucleotide, whereas the method in Examples 1 and3 is better suited to detecting total oligonucleotide.

The validation of the DNA ligase/ELISA method was performed in human plasma. A linear range of 0.05 nM to 20 nm ($r \geq 0.99$) was obtained in human plasma for ISIS 2302. This linear range was covered by two calibration curves (low and high). Analysis of blank plasma from 12 subjects indicated that there was no substantial endogenous interference with the detection of ISIS 2302. The assay was demonstrated to be specific, accurate, precise and sensitive for the quantitation of ISIS 2302 in human plasma. Moreover, the method was reproducible by multiple analysis.

Example 5

Specificity

Control human plasma from six subjects was analyzed in triplicate for possible endogenous interference. As shown in Table 5, plasma from four of the six subjects had responses less than 2% of the response at the LOQ (50 pM). However, two subjects showed high fluorescence signals 439% and 41.5% of LOQ). The reason for these high responses is unknown. Control human plasma from six additional subjects was studied. From the second specificity analysis, plasma from all six subjects had responses less than 11% of the response at the LOQ (50 pM). Therefore, the method was specific in the analysis of ISIS 2302 from human plasma.

TABLE 5

Specificity for the ELISA/ligation assay in control human plasma

| Subject ID | Calc. Conc. Equivalent 59 ISIS 2302 (Mean ± SD) | % LOQ |
|---|---|---|
| M76502 | <1 | <2 |
| M76505 | 219 ± 27.9 | 438.6 |
| M76509 | <1 | <2 |
| M75162 | <1 | <2 |
| M75194 | <1 | <2 |

TABLE 5-continued

Specificity for the ELISA/ligation assay in control human plasma

| Subject ID | Calc. Conc. Equivalent 59 ISIS 2302 (Mean ± SD) | % LOQ |
|---|---|---|
| M75152 | 21 ± 4.6 | 41.5 |
| M78444 | <1 | <2 |
| M78446 | <1 | <2 |
| M78449 | <1 | <2 |
| M78450 | <1 | <2 |
| M78451 | <5.5 | <10.9 |
| M78452 | <2.7 | <5.4 |

Example 6

Cross-reactivity Towards ISIS 2302 Metabolites

Figure 3:
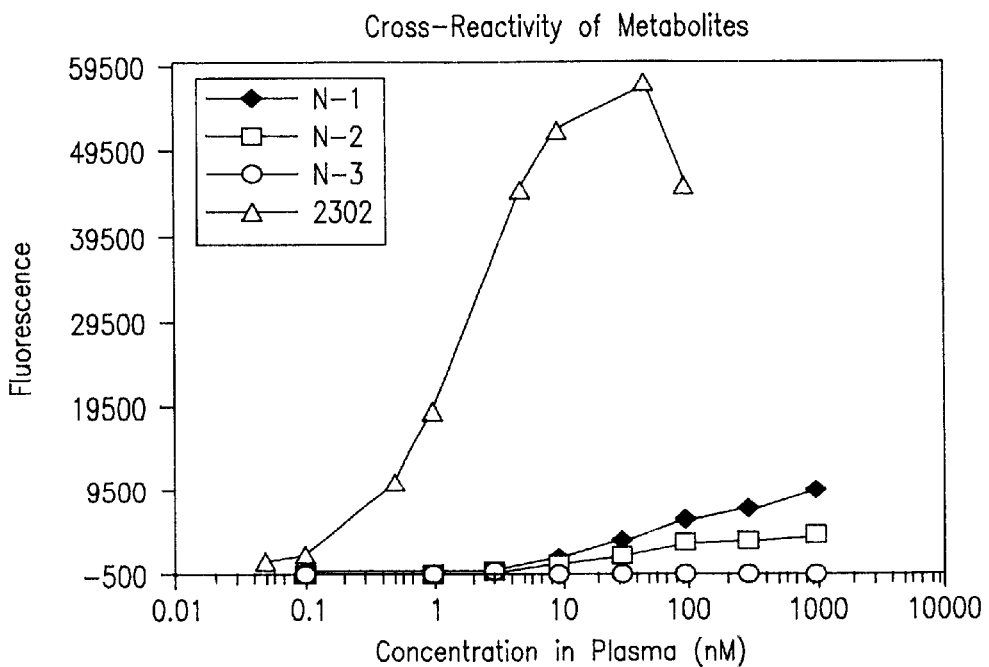
FIG. 3 is a graph showing the cross-reactivity of ISIS 2302 metabolites in human plasma.

The assay cross-reactivity towards the N-1 to N-3 metabolites was studied at the concentration range of 100 pM to 1 µM in duplicate in matrix. The N-1, N-2 and N-3 metabolites were shortened by synthesis of 1 to 3 fewer nucleotides, respectively, from the 3' end of ISIS 2302. The response curve for ISIS 2302 was studied at the concentration range of 50 pM to 0.1 µM in duplicate in matrix. As shown in FIG. 3, the fluorescence response generated from N-1 to N-3 was very minimal. Because fluorescence of metabolites at 50% maximum ISIS 2302 fluorescence response cannot be measured, the cross-reactivity was estimated at 10% of the maximal ISIS 2302 fluorescence response. The % cross-reactivity was about 0.22% for N-1 and was below 0.22% for N-2 and N-3.

Example 7

Linear Range

The calibration curve (50 to 2000 pM) in human plasma was run by two analysts on three different days. Each calibration curve was run in duplicate at concentrations of 50, 100, 200, 500, 1000, 1500 and 2000 pM. Each curve was fitted to log/log linear curve without weighting. Additional curves that were run in the study were also reported in Table 6. As shown in Table 6, correlation coefficients for ISIS 2302 were found to be greater than or equal to 0.99 for all of the calibration curves. Therefore, an acceptable linearity was achieved at concentrations that ranged from 50 to 2000 pM for ISIS 2302 in human plasma. A representative calibration curve is shown in FIG. 4.

TABLE 6

Summary of calibration curves for the analysis of ISIS 2302 in human plasma

| Date | Analyst | Range | y-int. | Slope | Correlation Coeff. ($r^2$) |
|---|---|---|---|---|---|
| 1 | 1 | 50 pM–2 nM | 1.4426 | 0.963 | 0.9977 |
| 2 | 1 | 50 pM–2 nM | 1.1368 | 1.0423 | 0.9963 |
| 3 | 1 | 50 pM–2 nM | 0.5344 | 1.2189 | 0.9960 |
| 4 | 1 | 50 pM–2 nM | 1.4428 | 0.9576 | 0.9951 |
| 5 | 2 | 50 pM–2 nM | 1.4839 | 0.9505 | 0.9910 |
| 6 | 1 | 50 pM–2 nM | 0.9725 | 1.0838 | 0.9937 |
| 7 | 1 | 1 nM–20 nM | 3.3895 | 0.8737 | 0.9912 |

Example 8

Intra-day Accuracy and Precision for Detection of ISIS 2302 in Plasma Using DNA Ligase/ELISA Assay Intra-day accuracy and precision was assessed from LOQ (50 pM), low (100 pM), medium (500 pM) and high (1500 pM) QC samples performed in human plasma. Six replicate QC samples were used. To verify the accuracy and precision of dilution samples, an extra high QC sample containing 5000 pM of ISIS 2302 in human plasma were prepared in six replicate. A 1:10 dilution was made for this QC sample diluted with blank human plasma prior to sample analysis. Concentrations of ISIS 2302 from the LOQ, low, medium, high and diluted QC samples were analyzed using the calibration curve method (Equation 1)

$$\text{Log}_{10}(C_2) = (\text{Log}_{10}(\text{Flu}) - \text{intercept})/\text{slope} \tag{1}$$

Where $C_2$=concentration of analyte (ISIS 2302) and Flu=fluorescence reading of the analyte. The intercept and slope were from linear regression of the calibration curve. Accuracy for the QC samples was calculated as the percentage of the calculated concentrations compared to the nominal concentrations for ISIS 2302 (% actual). Precision was expressed as coefficient of variation (% CV). The results are summarized in Table 7. Acceptable assay accuracy was achieved for ISIS 2302 (in the range of 102–122% of nominal spiked concentrations on Day 1, 92.3–121% on Day 2; and 78.3–107% on Day 3).

TABLE 7

Intra-day accuracy and precision for ISIS 2302 in human plasma (n = 6)

| ID | Date | Nominal Conc. (pM) | Mean observed conc. (pM) | SD observed conc. (pM) | Accuracy | % RSD |
|---|---|---|---|---|---|---|
| LOQ | 1 | 50 | 51 | 11 | 102.2 | 21.9 |
| Low QC | 1 | 100 | 112 | 20 | 111.6 | 18.1 |
| Mid QC | 1 | 500 | 608 | 77 | 121.7 | 12.7 |
| High QC | 1 | 1500 | 1642 | 90 | 109.5 | 5.5 |
| Dil. QC | 1 | 5000 | 6864 | 1024 | 137.3 | 14.9 |
| LOQ | 2 | 50 | 46 | 16 | 92.3 | 34.8 |
| Low QC | 2 | 100 | 102 | 12 | 101.5 | 11.8 |
| Mid QC | 2 | 500 | 604 | 66 | 120.9 | 10.9 |
| High QC | 2 | 1500 | 1601 | 164 | 106.7 | 10.2 |
| Dil. QC | 2 | 5000 | 5931 | 646 | 118.6 | 10.9 |
| LOQ | 3 | 50 | 39 | 27 | 78.3 | 69.6 |
| Low QC | 3 | 100 | 93 | 32 | 92.9 | 34.3 |
| Mid QC | 3 | 500 | 528 | 85 | 105.6 | 16.1 |
| High QC | 3 | 1500 | 1605 | 153 | 107.0 | 9.6 |
| Dil. QC | 3 | 5000 | 6815 | 863 | 136.3 | 12.7 |

Acceptable intra-day precision, expressed as relative standard deviation (% RSD was less than 18.1% for low, mid and high QCs) was obtained for ISIS 2302 with the exception of the low QC on day 3 (% RSD=34.8%). However, the LOQ showed high variability (% RSD in the range of 21.9–69.6%); therefore the limit of quantitation was raised to the new QC level, 100 pM (low QC). The accuracy (% actual) for ISIS 2302 for the diluted samples was in the range of 118.6–137.3% and did not meet the accuracy acceptance criteria. The % RSD for ISIS 2302 for the diluted samples was in the range of 10.9–14.9% and met the precision acceptance criteria. Therefore, in order to quantitate samples with higher plasma concentrations, the method was cross-validated to a high calibration curve as discussed below.

In summary, intra-day accuracy at LOQ (50 pM) met the accuracy acceptance criteria set in the protocol (80 to 120%) on days 1 and 2, and was at 78.3% on day 3. The precision for ISIS 2302 at the LLOQ, however, had a % RSD in the range of 21.9%–69.6% and did not meet the precision acceptance criteria set in the validation protocol. Therefore, the LLOQ was raised to the next QC level, 100 pM (low QC) as described in Example 9.

Example 9

Cross-validation to High Range in Human Plasma

From the dilution sample analysis of the intra-day accuracy and precision study, the accuracy deviated greater than 20% of the actual value in two out of three days. Therefore, samples over the calibration range cannot be accurately determined using a simple dilution. In order to determine these samples, a one-day cross-validation at high range was conducted.

In this validation procedure, a six-point calibration standard from 1 nm to 50 nM (at 1,2,5,10,20 and 50 nM) in duplicate were prepared and analyzed by the ELISA described in Example 4. Accuracy and precision were assessed with QC samples in six replicates at 1 nM (LOQ), 3 nM (low QC), 10 nM (medium QC) and 40 nM (high QC) prepared in human plasma. For sample preparation of the calibration standards and QC samples, 10 µL of standard solution was spiked into 10 µL of human plasma and 80 µL of distilled water.

The linear range for the high curve was 1 to 20 nM with $r^2$ at 0.9912. The 50 nM calibration standard fell off the curve, which may have resulted from depletion of the enzymatic substrate at 50 nM. As shown in Table 8, the accuracy and precision for the LOQ, low and medium QC met the established accuracy and precision acceptance criteria. However, the high QC had a % actual of 64.2% which may also have resulted from depletion of the enzymatic substrate. In summary, the cross-validation to a high calibration range indicated that the assay was accurate and precise for the quantitation of ISIS 2302 at concentrations between 1 and 10 nM in human plasma.

TABLE 8

Intra-day accuracy and precision for ISIS 2302 in human plasma at high concentrations (n = 6)

| Nominal Conc. (nM) | Calc. Conc. (nM) | Calc. Conc. (nM) (mean ± SD) | % Actual | % RSD |
|---|---|---|---|---|
| 1 | 1.12 | 0.90 ± 0.18 | 89.7 | 20.2 |
| 3 | 3.65 | 3.19 ± 0.50 | 106.5 | 15.6 |
| 10 | 11.3 | 10.5 ± 1.63 | 104.6 | 15.6 |
| 40 | 27.2 | 25.7 ± 2.00 | 64.2 | 7.79 |

Example 10

Inter-day Precision and Accuracy for ISIS 2302 in Human Plasma (n=18)

Inter-day accuracy and precision were calculated from the pooled data of QC using 18 replicates of QC samples each at four different concentrations (50,100,500 and 1500 pM) performed on three different days by two analysts. As shown in Table 9, inter-day accuracy for ISIS 2302 was in the range of 90.2–116% at LLOQ, low, medium and high QC concentrations. The inter-day precision at LOQ (50 pM) was 42.5%, which did not meet the precision acceptance criteria set in the validation protocol. As stated in the section of intra-day accuracy and precision, the LOQ was raised to the low QC level (100 pM). At the new LOQ (100 pM), the % RSD was 23.9%, which met the new established acceptance criteria ($\leq$25% at the LOQ). The inter-day precision for ISIS 2302 at medium and high QC concentrations (500 and 1500 pM) had % RSD of <14.0%, which met the precision acceptance criteria.

The dilution QC had an inter-day accuracy of 131% with % RSD of 14.1%. The observed concentration for the dilution QC was higher than expected, which resulted in a higher value of % actual. Therefore, a cross-validation to a higher calibration range was studied for the quantitation of higher concentrations of ISIS 2302 which may be present in human plasma. The inter-day data showed that the method was reproducible across multiple analysts.

TABLE 9

Inter-day accuracy and precision for ISIS 2302 in human plasma (n = 18)

| ID | Nominal conc. (pM) | Observed Conc. (pM) mean ± SD | Accuracy | % RSD |
|---|---|---|---|---|
| LOQ | 50 | 45 ± 19 | 90.2 | 42.5 |
| Low QC | 100 | 102 ± 24 | 102 | 23.9 |
| Mid QC | 500 | 580 ± 81 | 116 | 14.0 |
| High QC | 1500 | 1616 ± 133 | 108 | 8.2 |
| Dil. QC | 5000 | 6537 ± 919 | 141 | 14.1 |

Example 11

Stability of ISIS 2302 in Human Plasma

The stability of ISIS 2302 in human plasma was studied at low (100 pM) and high (1500 pM) oligonucleotide concentrations. Freeze/thaw, room temperature and long-term freezer storage stability were performed.

Freeze/thaw stability was studied for one and three freeze/thaw cycles, respectively. Thawing was studied at both room temperature (unassisted thawing) and at 37° C. in a water bath. At low concentrations (100 pM), the observed concentrations were 48% higher than the nominal concentration for both one and three cycles, thawing at both room temperature and at 37° C. (Table 10). At high concentrations (1500 pM), however, the observed concentrations of ISIS 2302 wherein the range of 92.5% to 108% of the nominal value after one and three cycles of freeze/thaw thawing at both room temperature and 37° C. It appeared that ISIS 2302 was not stable at 100 pM, but was stable at 1500 pM in human plasma after freeze/thaw cycles. Thawing temperature did not make a difference. The sulfur in ISIS 2302 may be exchanged to oxygen at low oligonucleotide concentrations by unknown mechanisms. Ligation efficiency is higher for phosphodiester than phosphorothioate, resulting in higher apparent concentrations. EDTA may slow this process.

TABLE 10

Freeze/thaw stability

| Nominal (pM) | Cycles | Thawing Temp. | Observed Conc. (pM) (Mean ± SD) | % Nominal | % RSD |
|---|---|---|---|---|---|
| 100 | 1 | RT | 159 ± 43 | 159 | 26.8 |
|  | 1 | 37° C. | 148 ± 42 | 148 | 28.6 |
|  | 3 | RT | 159 ± 14 | 159 | 8.51 |
|  | 3 | 37° C. | 182 ± 17 | 182 | 9.31 |
| 1500 | 1 | RT | 1414 ± 21 | 94.3 | 1.51 |
|  | 1 | 37° C. | 1620 ± 111 | 108 | 6.84 |
|  | 3 | RT | 1388 ± 77 | 92.5 | 5.55 |
|  | 3 | 37° C. | 1596 ± 138 | 106 | 8.62 |

Room temperature stability was studied at low (100 pM) and high (1500 pM) concentration stored at room temperature for 4 hr and 24 hr, respectively. At low concentrations 9100 pM), the observed concentrations were 56% and 24% higher than the nominal concentration for the 4 hr and 24 hr storage time point, respectively (Table 11). At high concentrations (1500 pM), however, the observed concentrations of ISIS 2302 were 95.3% and 105% of the nominal value concentration for the 4 hr and 24 hr storage time point, respectively.

TABLE 11

Room temperature stability

| Conc. (pM) | Storage time | Observed conc. (pM) (Mean ± SD) | % Nominal | % RSD |
|---|---|---|---|---|
| 100 | 4 hr | 156 ± 36 | 156 | 23.3 |
|  | 24 hr | 124 ± 15 | 124 | 11.8 |
| 1500 | 4 hr | 1430 ± 12 | 95.3 | 0.81 |
|  | 24 hr | 1575 ± 191 | 105 | 12.2 |

Long-term freezer stability was determined by storage of 100 pM and 1500 pM ISIS 2302 for one, three and six months. The results (Table 12) show that the oligonucleotide was stable at 1500 pM for 1, 3 and 6 months, and at 100 pM for 3 and 6 months, but not at 100 pM for one month.

TABLE 12

Long-term freezer stability

| Storage | Nominal (pM) | Observed conc. (pM) (Mean ± SD) | % Nominal | % RSD |
|---|---|---|---|---|
| 1 month | 100 | 142 ± 22 | 142 | 15.8 |
|  | 1500 | 1569 ± 161 | 105 | 10.2 |
| 3 month | 100 | 112 ± 6 | 112 | 5.14 |
|  | 1500 | 1479 ± 74 | 98.6 | 5.01 |
| 6 month | 100 | 79 ± 13 | 79.1 | 16.87 |
|  | 1500 | 1524 ± 105 | 101.6 | 6.91 |

What is claimed is:

1. A method for detecting or quantitating an oligonucleotide in a bodily fluid or extract, wherein said oligonucleotide comprises at least one modification, comprising the steps of:
- contacting said fluid or extract with a probe complementary to said modified oligonucleotide to form a hybrid, wherein said probe comprises a region at one end thereof which does not hybridize to said modified oligonucleotide;
- contacting said hybrid with an enzyme and a detectable label, wherein said enzyme directs the incorporation of said label into said modified oligonucleotide opposite said region of said probe which does not hybridize to said modified oligonucleotide; and
- detecting said label, wherein the presence of said label indicates the presence of said modified oligonucleotide.

2. The method of claim 1, wherein said bodily fluid is plasma.

3. The method of claim 1, wherein said modified oligonucleotide comprises a modification at the 2' position of at least one sugar moiety.

4. The method of claim 3, wherein said 2' modification is a 2'-O-methoxyethyl modification.

5. The method of claim 1, wherein said modified oligonucleotide comprises at least one modified base.

6. The method of claim 5, wherein said modified base is 5-methylcytosine.

7. The method of claim 1, wherein said label is calorimetric, radioactive, chemiluminescent, enzymatic or fluorescent.

8. The method of claim 1, wherein said label is digoxigenin.

9. The method of claim 1, wherein said enzyme is DNA polymerase.

10. The method of claim 1, wherein said oligonucleotide is exogenously administered.

11. A method for detecting or quantitating an oligonucleotide in a bodily fluid or extract, comprising the steps of:
- contacting said fluid or extract with a capture probe complementary to said oligonucleotide to form a hybrid, wherein said capture probe comprises a region at one end thereof which does not hybridize to said oligonucleotide;
- contacting said hybrid with a labeled detection probe complementary to said region of said capture probe which does not hybridize to said oligonucleotide in the presence of an enzyme which ligates the oligonucleotide and the detection probe; and
- detecting said label, wherein the presence of said label indicates the presence of said oligonucleotide.

12. The method of claim 11, wherein said bodily fluid is plasma.

13. The method of claim 11, wherein said oligonucleotide comprises at least one modification.

14. The method of claim 13, wherein said modified oligonucleotide comprises at least one modified internucleoside linkage.

15. The method of claim 11, wherein said oligonucleotide comprises a modification at the 2' position of at least one sugar moiety.

16. The method of claim 15, wherein said 2' modification is a 2'-O-methoxyethyl modification.

17. The method of claim 11, wherein said oligonucleotide comprises at least one modified base.

18. The method of claim 17, wherein said modified base is 5-methylcytosine.

19. The method of claim 11, wherein said label is calorimetric, radioactive, chemiluminescent, enzymatic or fluorescent.

20. The method of claim 11, wherein said label is digoxigenin.

21. The method of claim 11, wherein said enzyme is DNA ligase.

22. The method of claim 11, wherein said oligonucleotide is exogenously administered.

23. A method for detecting or quantitating an oligonucleotide in a bodily fluid or extract, wherein said oligonucleotide comprises at least one modification, comprising the steps of:
- contacting said fluid or extract with a capture probe complementary to said modified oligonucleotide and a second probe, wherein said capture probe comprises a detectable marker and a portion which binds to said modified oligonucleotide, and wherein said second probe comprises a first portion which binds to said detectable marker and a second portion which produces an overhanging flap upon binding to said modified oligonucleotide to form a complex;
- contacting said complex with a nuclease to cleave said flap; and
- detecting said flap.

24. The method of claim 23, wherein said bodily fluid is plasma.

25. The method of claim 23, wherein said modified oligonucleotide comprises a modification at the 2' position of at least one sugar moiety.

26. The method of claim 25, wherein said 2' modification is a 2'-O-methoxyethyl modification.

27. The method of claim 23, wherein said modified oligonucleotide comprises at least one modified base.

28. The method of claim 27, wherein said modified base is 5-methylcytosine.

29. The method of claim 23, wherein said nuclease is selected from the group consisting of eubacterial polA DNA polymerase, 5' to 3' exonuclease, 5' nuclease associated with bacteriophage T5, FEN1, RAD2 and xeroderma pigmentosum-complementation group G endonuclease homologs from eukaryotes.

30. The method of claim 23, wherein said oligonucleotide is exogenously administered.

31. The method of claim 1, wherein said modified oligonucleotide comprises at least one modified internucleoside linkage.

32. The method of claim 23, wherein said modified oligonucleotide comprises at least one modified internucleoside linkage.

33. The method of claim 31, wherein said internucleoside linkage is a phosphorothioate linkage.

34. The method of claim 32, wherein said modified internucleoside linkage is a phosphorothioate linkage.

35. The method of claim 14, wherein said internucleoside linkage is a phosphorothioate linkage.

* * * * *